(12) United States Patent
Gershony et al.

(10) Patent No.: US 6,296,658 B1
(45) Date of Patent: Oct. 2, 2001

(54) VASCULAR SEALING APPARATUS

(75) Inventors: Gary Gershony, El Macero, CA (US); Daniel J. Kasprzyk, Fogelsville, PA (US); Michael J. Horzewski, San Jose, CA (US)

(73) Assignee: Vascular Solutions, Inc., Minneapolis, MN (US)

( * ) Notice: Subject to any disclaimer, the term of this patent is extended or adjusted under 35 U.S.C. 154(b) by 0 days.

(21) Appl. No.: 09/491,108

(22) Filed: Jan. 25, 2000

Related U.S. Application Data

(63) Continuation of application No. 08/877,255, filed on Jun. 17, 1997, now Pat. No. 6,017,359, which is a continuation of application No. 08/549,430, filed on Oct. 27, 1995, now abandoned, which is a continuation-in-part of application No. 08/303,088, filed on Sep. 8, 1994, now abandoned, which is a continuation of application No. 08/067,213, filed on May 25, 1993, now Pat. No. 5,383,896.

(51) Int. Cl.[7] ............................................. A61B 17/58
(52) U.S. Cl. ................................. 606/213; 608/192
(58) Field of Search ................................. 606/159, 213, 606/169, 139, 140, 141–145, 192; 604/178, 256

(56) References Cited

U.S. PATENT DOCUMENTS

| | | |
|---|---|---|
| 802,190 | 10/1905 | Heineman . |
| 1,191,736 | 7/1916 | Roberson . |
| 1,794,221 | 2/1931 | Washburn et al. . |
| 2,169,947 | 8/1939 | Freudenberg . |
| 2,492,458 | 12/1949 | Bering, Jr. . |
| 2,533,004 | 12/1950 | Ferry et al. . |
| 2,862,497 | 2/1958 | Pagano . |
| 2,898,913 | 8/1959 | Ritter et al. . |
| 3,016,895 | 1/1962 | Sein . |
| 3,056,408 | 10/1962 | Brown . |
| 3,447,533 | 6/1969 | Spicer . |
| 3,516,403 | 6/1970 | Cournut . |

(List continued on next page.)

FOREIGN PATENT DOCUMENTS

| | | |
|---|---|---|
| 8907370 | 9/1989 | (DE) . |
| 0476178A1 | 3/1992 | (EP) . |
| 0482350A2 | 4/1992 | (EP) . |
| 0493810A1 | 7/1992 | (EP) . |
| 2641692 | 7/1980 | (FR) . |
| 1509023 | 4/1978 | (GB) . |
| 1569660 | 6/1980 | (GB) . |
| 2057269 | 4/1981 | (GB) . |
| WO89/11301 | 11/1989 | (WO) . |
| WO90/14796 | 12/1990 | (WO) . |
| WO91/09641 | 7/1991 | (WO) . |
| WO92/22252 | 12/1992 | (WO) . |
| WO93/07928 | 4/1993 | (WO) . |

OTHER PUBLICATIONS

Bierman, et al., "Portal Venipuncture. A Percuntaneous, Trans–hepatic Approach," *Proceedings of the Society for Experimental Biology and Medicine*, vol. 79, No. 3, pp. 550–552, Mar. 1952.

(List continued on next page.)

*Primary Examiner*—Gary Jackson
(74) *Attorney, Agent, or Firm*—Fredrikson & Byron, P.A.

(57) ABSTRACT

A device for sealing an opening or puncture in the wall of a blood vessel or other percutaneous openings. The device includes a shaft section member of a small diameter, with an expandable balloon and atraumatic tip at its distal end. The proximal end of the device has an inflation/deflation port which is utilized to inflate the balloon once it is in place within the blood vessel or other body cavity. The entire device is placed through a hemostasis vascular introducer or sheath, which is used during invasive percutaneous vascular procedures. The balloon is inflated and withdrawn until it engages the inner surface of the blood vessel. A procoagulant is injected via the introducer to the puncture. After a predetermined time period, the balloon is deflated and the device is withdrawn.

16 Claims, 2 Drawing Sheets

U.S. PATENT DOCUMENTS

| | | |
|---|---|---|
| 3,540,431 | 11/1970 | Mobin-Uddin . |
| 3,572,335 | 3/1971 | Robinson . |
| 3,675,639 | 7/1972 | Cimber . |
| 3,728,207 | 4/1973 | Heling . |
| 3,766,924 | 10/1973 | Pidgeon . |
| 3,800,792 | 4/1974 | McKnight et al. . |
| 3,903,882 | 9/1975 | Augurt . |
| 3,972,328 | 8/1976 | Chen . |
| 4,016,877 | 4/1977 | Cruz, Jr. et al. . |
| 4,060,081 | 11/1977 | Yannas et al. . |
| 4,066,083 | 1/1978 | Ries . |
| 4,080,970 | 3/1978 | Miller . |
| 4,148,664 | 4/1979 | Cruz et al. . |
| 4,167,945 | 9/1979 | Gottlieb . |
| 4,215,686 | 8/1980 | Gregory et al. . |
| 4,238,480 | 12/1980 | Sawyer . |
| 4,341,207 | 7/1982 | Steer et al. . |
| 4,347,841 | 9/1982 | Benyó et al. . |
| 4,390,519 | 6/1983 | Sawyer . |
| 4,404,970 | 9/1983 | Sawyer . |
| 4,407,787 | 10/1983 | Stemberger . |
| 4,516,968 | 5/1985 | Marshall et al. . |
| 4,555,242 | 11/1985 | Saudager . |
| 4,576,817 | 3/1986 | Montgomery et al. . |
| 4,578,067 | 3/1986 | Cruz, Jr. . |
| 4,606,910 | 8/1986 | Sawyer . |
| 4,614,794 | 9/1986 | Easton et al. . |
| 4,650,466 | 3/1987 | Luther . |
| 4,655,210 | 4/1987 | Edenbaum et al. . |
| 4,655,211 | 4/1987 | Sakamoto et al. . |
| 4,669,474 | 6/1987 | Barrows . |
| 4,676,782 | 6/1987 | Yamamoto et al. . |
| 4,701,163 | 10/1987 | Parks . |
| 4,725,671 | 2/1988 | Chu et al. . |
| 4,738,225 | 4/1988 | Goble et al. . |
| 4,774,091 | 9/1988 | Yamahira et al. . |
| 4,775,585 | 10/1988 | Hagiwara et al. . |
| 4,784,653 | 11/1988 | Bolton et al. . |
| 4,789,401 | 12/1988 | Ebinger et al. . |
| 4,793,351 | 12/1988 | Landman et al. . |
| 4,841,962 | 6/1989 | Berg et al. . |
| 4,847,049 | 7/1989 | Yamamoto . |
| 4,856,504 | 8/1989 | Yamamoto et al. . |
| 4,867,748 | 9/1989 | Samuelsen . |
| 4,892,519 | 1/1990 | Songer et al. . |
| 4,897,081 | 1/1990 | Poirier et al. . |
| 4,911,898 | 3/1990 | Hagiwara et al. . |
| 4,915,694 | 4/1990 | Yamamoto et al. . |
| 4,925,924 | 5/1990 | Silver et al. . |
| 4,994,033 | 2/1991 | Shocket et al. . |
| 5,021,059 | 6/1991 | Kensey et al. . |
| 5,041,093 | 8/1991 | Chu . |
| 5,049,132 | 9/1991 | Shaffer et al. . |
| 5,060,642 | 10/1991 | Gilman . |
| 5,085,646 | 2/1992 | Svenson et al. . |
| 5,098,397 | 3/1992 | Svensson et al. . |
| 5,123,914 | 6/1992 | Cope . |
| 5,129,882 * | 7/1992 | Weldon et al. ............... 604/96 |
| 5,156,592 | 10/1992 | Martin et al. . |
| 5,156,595 | 10/1992 | Adams . |
| 5,159,937 | 11/1992 | Tremulis . |
| 5,192,300 | 3/1993 | Fowler . |
| 5,192,302 | 3/1993 | Kensey et al. . |
| 5,207,651 | 5/1993 | Snyder . |
| 5,213,567 | 5/1993 | Masaki . |
| 5,304,184 * | 4/1994 | Hathaway et al. ............ 606/144 |
| 5,308,313 | 5/1994 | Karami et al. . |
| 5,443,481 * | 8/1995 | Lee .............................. 606/213 |
| 5,916,236 * | 6/1999 | Van de Moer et al. ....... 606/213 |

OTHER PUBLICATIONS

Berkowitz, et al., "New Technique for Control of Ruptured Abdominal Aortic Aneurysm," *Surgery, Gynecology & Obstetrics*, pp. 107–109, Jul. 1971.

Arbulu, et al., "Control of Bleeding from a Gunshot wound of the Inferior Vena Cava at its Junction with the Right Atrium by Means of a Foley Catheter," The Journal of Thoracic and Cardiovascular Surgery, vol. 63, No. 3, pp. 427–429, Mar. 1972.

Okuda, et al., "Percutaneous Transhepatic Catherization of the Portal Vein for the Study of Portal Hemodynamics and Shunts," *Gastroenterology*, vol. 72, No. 2, pp. 279–284, Aug. 1977.

Viamonte, Jr. et al, "Selective Catherization of the Portal Vein and its Tributaries," *Radiology*, vol. 114, pp. 457–460, Feb. 1975.

Takayasu, et al., "Intrahepatic Portal Vein Branches Studied by Percutaneous Transphatic Portography," *Radiology*, vol. 154, No. 1, pp. 31–36, Jan. 1985.

Lunderquist, et al., "Transhepatic Catherterization and Obliteration of the Coronary Vein in Patients with Portal Hypertension and Esophageal Varices," *The New England Journal of Medicine*, vol. 291, No. 13, pp. 646–649, Sep. 26, 1974.

Scott, et al., "Percutaneous Transhepatic Obliteration of Gastro–Esophageal Varices," *The Lancet*, pp. 53–55, Jul. 10, 1976.

Thomas, "Control of Bleeding in Complicated Peripheral Vascular Lesions," *Surgery, Gynecology & Obstetrics*, pp. 1015–1018, Jun. 1971.

Takayasu, et al, "A New Hemostatic Procedure for Percutaneous Transhepatic Portal Vein Catheterization," *Japanese Journal of Clinical Oncology*, vol. 18, No. 3, pp. 227–230, 1988.

Gupta, et al., "The Role of Intra–aortic Balloon Occlusion in Penetrating Abdominal Trauma," *The Journal of Trauma*, vol. 29, No. 6, pp. 861–865, Jun. 1989.

McAnena, et al., "Insertion of a Retrohepatic Vena Cava Balloon Shunt Through the Saphenofemoral Junction," *The American Journal of Surgery*, vol. 158, No. 5, pp. 463–466, Nov. 1989.

Tobin, et al., "Plugged Liver Biopsy in Patients with Imparied Coagulation," *Digestive Diseases and Sciences*, vol. 34, No. 1, pp. 13–15, Jan. 1989.

Pfab, et al., "Local Hemostatis of Nephrostomy Tract with Fibrin Adhesive Sealing in Percutaneous Nephrolithotomy," *European Urology*, vol. 13, pp. 118–121, 1987.

Abbott, et al., "Microcrystalline Collagen as a Topical Hemostatic Agent for Vascular Surgery," *Surgery*, vol. 75, No. 6, pp. 926–933, Jun. 1974.

Silverstein, et al., "Experimental and Clinical Experiences with Collagen Fleece as a Hemostatic Agent," *The Journal of Trauma*, vol. 21, No. 5, pp. 388–393, May 1981.

Chvapil, et al., "Experimental Experiences with the Collagent Sponge as Hemostaticum and Tampon," *Journal of Biomedical Material and Research*, vol. 2, pp. 245–264, 1968.

Allison, et al., "Percutaneous Liver Biopsy and Track Embolization with Steel Coils," *Radiology*, vol. 169, No. 1, pp. 2610–2663, Oct. 1988.

Chvapil, et al., "Medical and Surgical Applications of Collagen, " pp. 1–61, undated.

Behl, et al., "Treatment of Carotid–Cavernous Fistulas with Detatchable Balloon Catheter Occlusion," *Advances in Opthalmic, Plastic, and Reconstructive Surgery*, vol. 7, pp. 157–165, 1987.

Katzen, et al., "Treatment of Carotid–Cavernous Fistulas with Detachable Balloon Catheter Occlusion," *Advances in Ophthalmic, Plastic, and Reconstructive Surgery*, vol. 7, pp. 157–165, 1987.

Gallo, et all, "A Safe Technique for Removal of Massive Left Atrial Thrombus," *The Annals of Thoracic Surgery*, vol. 31, No. 3, pp. 283–284, Mar. 1981.

Ong, "Removal of Blunt Oesophageal Foreign Bodies in Children Using a Foley Catheter," *Australian Paediatric Journal*, vol. 18, No. 1, pp. 60–62, Mar. 1982.

Yellin, et al., "Vascular Isolation in Treatment of Juxtahepatic Venous Injuries," *Archives of Surgery*, vol. 102, No. 6, pp. 566–573, Jun. 1971.

Rösch, et al., "Experimental Catheter Obstruction of the Gastric Coronary Vein, Possible Technique for Percutaneous Intravascular Tamponade of the Gastroesophageal Varices," *Investigative Radiology*, vol. 10, No. 3, pp. 206–211, May-Jun. 1975.

Doty, et al., "Control of Hepatic Venous Bleeding By Transvenous Balloon Catheter," *Surgery, Gynecology & Obstetrics*, pp. 449–452, Sep. 1970.

Ansari, et al., "Foley Catheter for Salpingography, Pneumonograph, Tubal Insufflation, and Hydrotubation," *Obstetrics and Gynecology*, vol. 50, No. 1, pp. 108–112, Jul. 1977.

Gembarowicz, et al., "Management of Variceal Hemorrhage," *Archives of Surgery*, vol. 115, No. 10, pp. 1160–1164, Oct. 1980.

Gazzelle, et al., "Hemostatic Protein–Polymer Sheath: New Method to Enhance Hemostasis at Percutaneous Biopsy," *Radiology*, vol. 175, No.3, pp. 671–674, Jun. 1990.

Hoyman, et al., "Hydrocolloid Wafer Dressings and Arterial Catheter Access Sites," *Ostomy/Wound management*, pp. 22–27, Spring 1989.

Bhatnagar, et al., "Composites of Collagen with Synthetic Polymers for biomedical Applications," *Advanced Concepts*, pp. 179–184, undated.

Gazelle, et al., "Hemostatic Protein Polymer Sheath: Improvement in Hemostatsis at Percutaneous Biopsy in the Settling of Platelet Dystunction," *Radiology*, vol. 187, No. 1, pp. 269–272, Apr. 1993.

Richarson, et al., "Peripheral Vascular Complications of Coronary Angioplasty," *The American Surgeon*, vol. 55, No. 11, pp. 675–680, Nov. 1989.

Cox, et al., "'How I Do It'—Head and Neck and Plastic Surgery, A Targeted Problem and its Solution, A Hemostatic Device for Endoscopic Surgery," *Laryngoscope*, vol. 98, No. 5, p. 579, May 1988.

Debrun, et al., "Two Different Calibrated–Leak Balloons: Experimental Work and Application in Humans," *American Journal of Neuroradiology*, vol. 3, pp. 407–414, Jul. Aug. 1982.

Ruff, et al., "Percutaneous Vascular Intervention after Surgical Shunting for Portal Hypertension," *Radiology*, vol. 164, No. 2, pp. 469,74, Aug. 1987.

Panés, et al., "Efficacy of Balloon Tamponade in Treatment of Bleeding Gastric and Esophageal Varices Results in 151 Consecutive Episodes," *Digestive Diseases and Sciences*, vol. 33, No. 4, pp. 454–459, Apr. 1988.

Nguyen, et al., "Treatment of Coronary Artery Stenosis and Coronary Arteriovenous Fistula by Interventional Cardiology Techniques," *Catheterization and Cardiovascular Diagnosis*, vol. 18, No. 4, pp. 240–243, Dec. 1989.

Radout, III, et al., "Hepatoportal Arteriovenous Fistula Treated with Detachable Balloon Emolotherapy," *The American Journal of Gastroenterology*, vol. 84, No. 1, pp. 63–66, Jan. 1989.

Chuang, et al., "Sheath Needle for Liver Biopsy in HighRisk Patients," *Radiology*, vol. 166, No. 1, pp. 261–262, Jan. 1988.

Chvapil, et al., "A Standardized Animal Model for Evaluation of Hemostatic Effectiveness of Various Materials," *The Journal of Trauma*, vol. 23, No. 12, pp. 1042–1047, Dec. 1983.

Silverstein, et al., "Collagen Fibers as a Fleece Hemostatic Agent," *The Journal of Trauma*, vol. 20, No. 8, pp.688–694, Aug. 1980.

Abbott, et al., "the Effectiveness and Mechanism of Collagen–Induced Topical Hemostatsis," *Surgery*, vol. 78, No. 6, pp. 723–729, Dec. 1975.

Riley, et al., "Percutaneous Liver Biopsy with Plugging of Needle Track: A Safe Method for Use in Patients with Imparied Coagulation," *The Lancet*, No. 8400, p. 436, Aug. 25, 1984.

\* cited by examiner

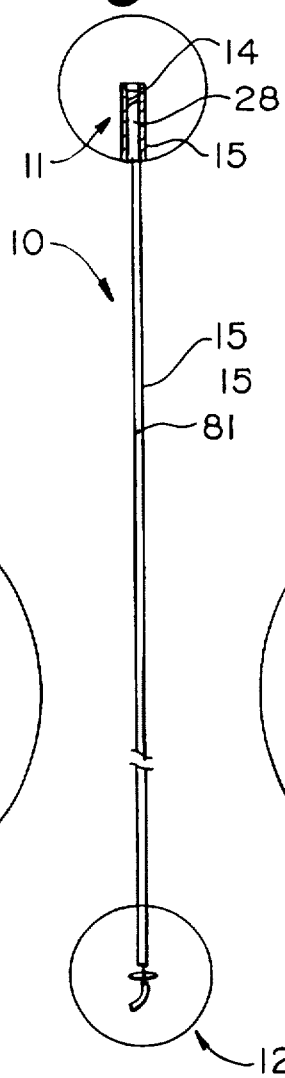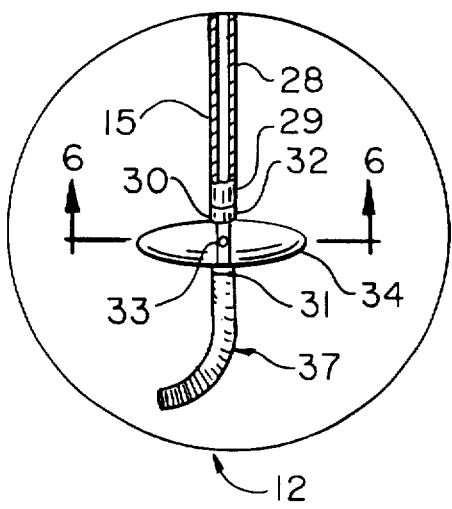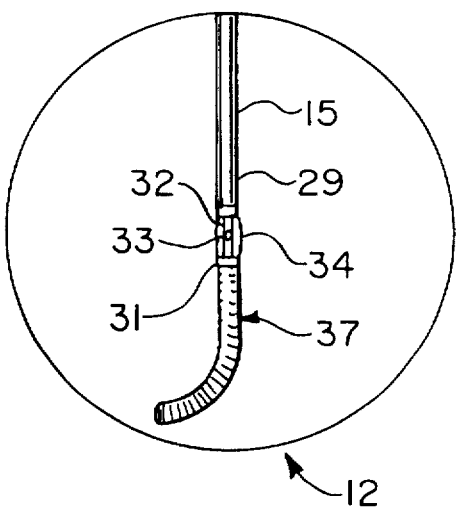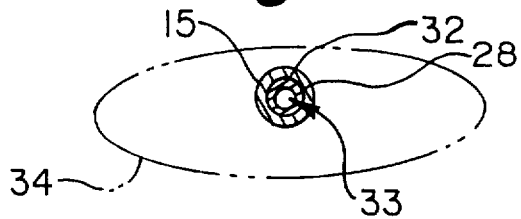

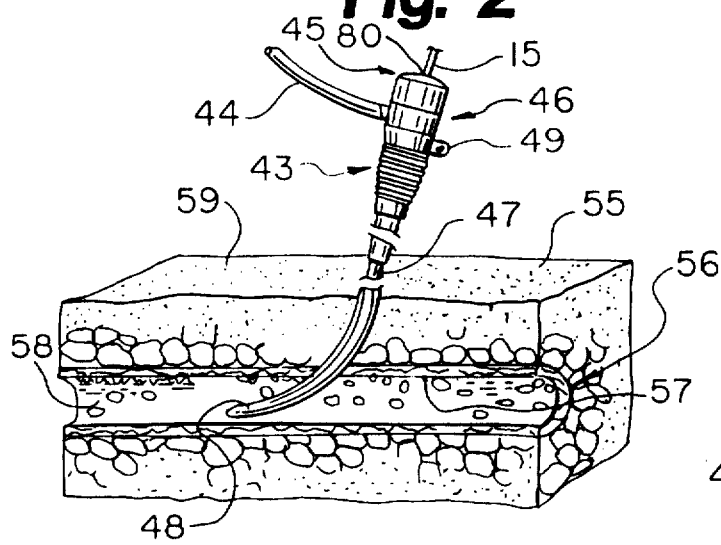
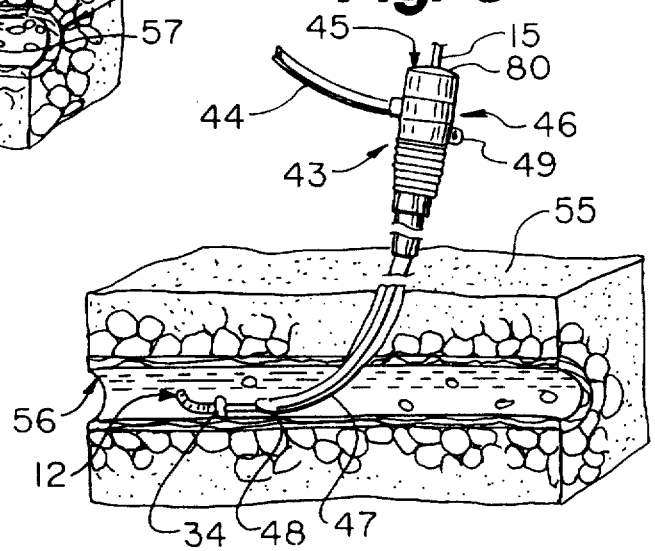
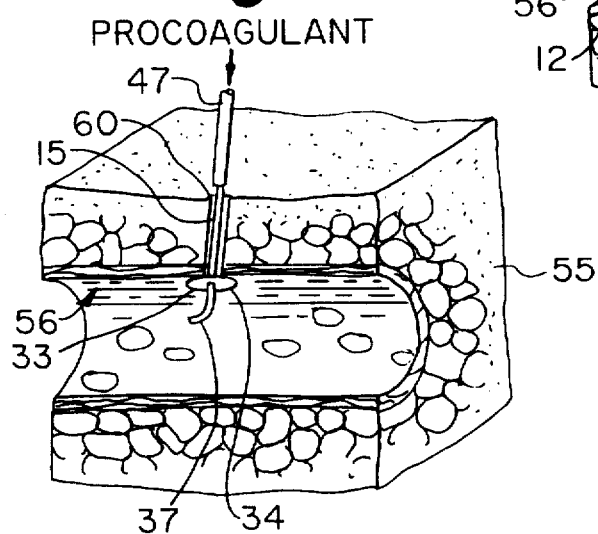
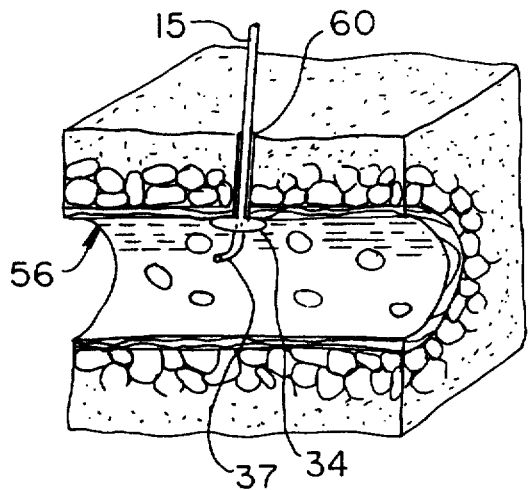

VASCULAR SEALING APPARATUS

CROSS-REFERENCES TO RELATED APPLICATIONS

This is a Continuation Division of application Ser. No. 08/877,255, filed Jun. 17, 1997, now U.S. Pat. No. 6,017, 359, issued Jan. 25, 2000, which in turn is a continuation of application Ser. No. 08/549,430, filed Oct. 27, 1995 now abandoned, which in turn is a continuation-in-part of application Ser. No. 08/303,088, filed Sep. 8, 1994 now abandoned, which is a continuation of application Ser. No. 08/067,213, filed May 25, 1993, now U.S. Pat. No. 5,383, 896, issued Jan. 24, 1995.

BACKGROUND OF THE INVENTION

1. Field of the Invention

This invention relates to medical devices in general and, more particularly, to hemostatic devices. The device is particularly useful for arresting the flow of blood or hemorrhage from punctures of the vascular system.

2. Background Art

Various surgical procedures are performed by medical specialists such as cardiologists, utilizing percutaneous entry into a blood vessel or body cavity. Examples of such procedures include different techniques to recanalize atherosclerotic blood vessels, such as balloon angioplasty or atherectomy. Recently, both the types and number of procedures performed utilizing the above mentioned percutaneous access to blood vessels have increased greatly.

These procedures generally involve the percutaneous puncture with a thin walled needle into a blood vessel. Following this, a guidewire is placed through the needle into the blood vessel and the needle is withdrawn. An intravascular sheath of variable size is then advanced over the guidewire, percutaneously, into the lumen of the blood vessel. The introducer sheath is then used as an ingress/egress means during the procedure. Following completion of the procedure, the introducer sheath may be removed, but this requires the application of prolonged manual pressure over the puncture site by a physician or other suitably trained medical personnel The time involved here is frequently extensive since patients are often treated with a variety of anticoagulant and thrombolytic agents, particularly in the setting of a heart attack. Alternatively, the sheath may be left in the puncture site for a prolonged period of time until the patient's coagulation status has returned to normal Depending on the size of the vascular sheath, there may be an increased risk of bleeding to the patient, which may require blood transfusion. In addition, there is a significant risk for injury to the blood vessel upon removal of the sheath, particularly if the sheath has been in place for a prolonged period of time. This includes the possible development of an pseudo-aneurysm or severe hematoma. The current technique for removal of introducer sheaths is also painful to the patient and requires prolonged bed rest after removal This adds to the discomfort for the patient, as well as prolonging hospitalization and costs.

Many of the intra-vascular procedures are performed in patients who are clinically unstable or who have the potential to become so, following completion of the procedure. Following removal of the vascular access sheath, it could be cumbersome and sometimes difficult to re-enter the blood vessel if necessary. Thus, with the current technique for removal of the sheath following the procedure, no easy, reliable method is available to allow reaccess to the lumen of the blood vessel, if necessary.

In the past, various devices and methods have been used and proposed in an attempt to seal punctures in blood vessels by injection of a resorbable hemostatic plug into the puncture site, including U.S. Pat. Nos. 4744364 (Kensey), 4,852, 568 (Kensey), and 4,890,612 (Kensey).

Despite the need for a device and method which overcome the imitations and problems of the prior art, none insofar as is known, has been proposed or developed.

SUMMARY OF THE INVENTION

This invention provides a device for sealing an opening or puncture in the wall of a blood vessel. The device includes a shaft section of small diameter, with an expandable balloon and guidewire tip at its distal end. The proximal end of the device has a low profile port which is utilized to inflate and deflate the distal balloon once it is in place within the blood vessel, and which permits removal of a standard hemostasis introducer which is preexisting in the puncture. The introducer is used to inject a procoagulant to the puncture site, proximally with respect to the balloon for sealing.

Unique aspects of this invention include: (1) the creation of immediate hemostasis at the puncture site for procoagulant delivery; (2) the device balloon acts as a marker for delivery of procoagulant; (3) balloon approach prevents injection of procoagulant into the bloodstream; and (4) the apparatus and method allow reaccess to the patient's vasculature. Other features, benefits and objects of this invention will become clear from the following description by reference to the drawings.

BRIEF DESCRIPTION OF THE DRAWINGS

FIG. 1 is a perspective view of a vascular sealing device of the present invention, with segments enlarged to show details of the distal and proximal ends thereof FIG. 2 is a view of the vascular sealing device inserted through an introducer sheath and into a patient's vascular system, which is shown enlarged and in section.

FIG. 3 is a view of the vascular sealing device inserted through a vascular sheath, and being inflated.

FIG. 4 is a view of the vascular sealing device with its balloon portion inflated, and further showing removal of the vascular sheath.

FIG. 5 is a view of the vascular sealing device with the balloon inflated and being pulled firmly up against the inner surface of a vascular puncture.

FIG. 6 is a crossectional view of the apparatus taken along line 6—6 of FIG. 1a.

DESCRIPTION OF THE PREFERRED EMBODIMENT

Referring to FIGS. 1 and 6, a preferred form is shown of the vascular sealing device 10 for effecting closure of a puncture in a blood vessel which has been entered through percutaneous techniques. The device 10 is useable with a procoagulant which is injected through a standard percutaneous vascular sheath or introducer. The vascular sealing device 10 is shown to have an elongated thin, generally tubular body or conduit 15 with proximal and distal ends 11 and 12, respectively. Basically, the proximal end 11 of the device 10 is for physician manipulation and connection to associated medical apparatus described further below, while the distal end 12 is for insertion into the patient's body. Located at the proximal end 11 of device 10 is an inflation/deflation port 14.

The body member 15 has a tubular structure constructed of hypotubing or a similar material This structure also has a cylindrical and thin outer body wall with a central, continuous, and longitudinally extending lumen 28. The body member 15 has an outside diameter preferably not greater than 0.038 inches (0.965 mm.). The body 15 is semi-flexible and, importantly, has a predetermined rigidity such that central lumen 28 integrity is maintained. This is particularly important during longitudinal translational manipulation by the physician, through vascular introducer means (described below), into a percutaneous puncture in the patient's skin. The hypotubing of the body 15 is preferably constructed of a metallic material such as stainless steel, for example. Alternatively, the body 15 may be constructed of a polymeric material The body member 15 is shown to have a length preferably of at least 11.79 inches (30 cm).

The proximal end 11 of the lumen or hollow interior 28 is sealed with elastomeric material, preferably silicone, to form an inflation/deflation port 14. The seal forms the inflation/deflation port 14 by adhering to the internal wall surfaces of the proximal end 11 of body 15. The seal is of sufficient strength to maintain a pressure difference between the internal lumen 28 and the proximally disposed exterior of the seal This pressure difference is of a magnitude sufficient to maintain inflation of the balloon 34, which is in continuity with the lumen 28. The inflation/deflation port 14 is utilized by piercing its proximal face, preferably with a syringe needle, to a depth which allows the needle lumen to be in continuity with the lumen 28. An external syringe, attached to the proximal end of the needle, provides a piston means by which a gas or liquid is pumped into the balloon 34 for inflation, or out of the balloon 34 for deflation. Removal of the needle from the inflation/deflation port 14 causes the seal to re-establish the pressure differential barrier.

The structure of the proximal end 11 also allows the user to later slide a standard vascular sheath over the device body 15 and then to advance it to the puncture site for positioning within the blood vessel lumen. This allows reentry into the blood vessel, if necessary, for a further interventional procedure.

The bottom or distal end 12 of the device body 15 is shown to have a distal tip 29. The distal tip 29 further has an inset segment 32. The inset segment 32 has a tubular configuration and is oriented coaxially with respect to the distal tip 29. The inset segment 32 preferably has a diameter which is less than that of the distal tip 29 and a length equivalent to that of the wall of the balloon 34 when deflated. Thus, an inset with respect to the distal tip 29 is formed by this structure. The lumen 28 extends into the inset segment 32 and is communicatively connected to an orifice 33, which is disposed in the side wall of the inset segment 32. The orifice 33 is shown to have a circular configuration.

Referring to FIGS. 1A and B, the balloon 34 is disposed about the inset segment 32. In an uninflated state, the balloon 34 has a tubular configuration and is sealingly secured at each of its ends to respective ends 30 and 31 of the inset segment 32. Sealing securement may be made by various methods, including adhesives, ultrasonic welding, and compression fitting. The uninflated diameter of the balloon 34 is such that it is disposed substantially within the recess space formed by the difference in diameter of the inset segment 32 and the distal tip 29. This provides a low profile device diameter which reduces vascular trauma and puncture site diameter upon removal. In an inflated state the balloon 34 preferably assumes a rounded configuration, for example elliptical with a minimum inflated diameter of two times the french size of the introducer sheath puncture hole being sealed. In addition, the height or thickness of the inflated balloon 34 is preferably less than one half the diameter of a typical blood vessel being sealed, so as to minimize obstruction of flow through the blood vessel The balloon 34 is preferably constructed of an expandable material such as natural latex.

A flexible atraumatic extension 37 is shown disposed at the distal end 12 of the vascular sealing device 10, extending from the inset segment 32. The extension 37 preferably has a tubular structure with a diameter equivalent to that of the distal tip 29. Importantly, the extension 37 is formed of a flexible material such as guidewire as known in the art. The extension 37 is shown to have an end portion which is preferably curved in its inoperative state. This structure decreases the level of trauma to the vessel wall during insertion and manipulation of the device 10.

Referring to FIG. 1, 81 refers to a distance marker upon body 15 for the purpose of indicating to the user that the balloon 34 is distal to the sheath taper end 48 shown in FIGS. 2 and 3. By alignment of marker 81 at the top of the hemostatic valve opening at cap 45, proper location of the balloon 34 with respect to sheath tapered end 48 is assured.

Referring generally to FIGS. 2–5, in use, the vascular sealing device 10 is inserted into the input end 45 of an introducer or vascular sheath device 43 which has been previously positioned within the lumen 58 of a blood vessel 56. The typical introducer 43, as is well known, comprises a body structure 46, an elongated sheath 47 with a tapered end 48, a hemostatic ingress/egress valve 80 within a cap 45, an auxiliary tube 44 and a suture connector 49 which may be used to maintain the introducer 43 in an operative position on the patient's skin surface 55 for prolonged periods of time and to thereby permit reaccess to the patients vascular system 56. The body 46 of the introducer 43 remains on the exterior of the patient's body at all times, while the sheath 47 extends through puncture 60 in the skin surface 55, tissue 59, and vessel wall 57.

The vascular sealing device 10 is first inserted through the valve or gasket 80 of the introducer 43, distal end 12 first, and is advanced by physician manipulation of the body member 15, primarily, until the distal end 12 extends just beyond the distal tapered tip 48 of the sheath 47. Next, an inflator such as a syringe (not shown) pierces the inflation/deflation port 14 of device 10. Fluid or gas is advanced into the device 10 until a predetermined amount of balloon 34 inflation is attained. Then, the inflating means is removed. Next, the inflated balloon section 34 is pulled up against the vessel wall 56 at the puncture site 60, by manipulating the body member 15. At this point in the procedure, a hemostatic seal is effected at the puncture site 60. Next, and importantly, a procoagulant is injected through a fluid access port 44 of the introducer 43 and is released out its distal end 48 at the puncture site 60. Next, the introducer sheath 47 is withdrawn by manipulation of the introducer body 46 and sheath 47 proximal end. The balloon section 34 remains abutted against the inner intraluminal surface 56 of the puncture site 60. After a predetermined time period, on the order of 1–3 minutes, the balloon 34 is deflated and the device 10 is pulled proximally out of the puncture site 60.

The procoagulant may include one of the following substances or combinations of substances: (1) thrombin, (2) collagen, (3) fibrin/fibrinogen, (4) cyanoacrylate, (5) thrombin and collagen, (6) fibrin/fibrinogen and collagen, (7) cyanoacrylate and collagen, and (8) thrombin and fibrin/fibrinogen.

The advantages of the device 10 and method of the present invention include, but are not limited to, both individually and cooperatively, (1) that the inflated balloon 34 blocks egress of blood immediately upon being properly positioned in blood vessel at the puncture site to provide fast hemostasis; (2).that the inflated balloon 34 acts as an internal marker to permit the user to accurately gauge the depth of the puncture and the thickness of the tissues surrounding the puncture; and (3) that the inflated balloon 34 acts as a backstop at the inner wall of the blood vessel to (i) precisely position the sealing clot in the puncture and (ii) to prevent procoagulant from entering the patient's circulatory system.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

The invention claimed is:

1. A medical sealing apparatus for sealing a blood vessel aperture in a patient, comprising:
   a. a thin, elongated conduit having a central lumen, said conduit having proximal and distal ends, said conduit distal end being insertable into the blood vessel aperture and having an inflation segment including an external orifice which is communicatively connected to said lumen;
   b. an expandable member sealingly disposed at said conduit distal end inflation segment, said expandable member being inflatable with a fluid to a predetermined diameter;
   c. means to connect said conduit lumen to an external inflation source, said means to connect being disposed at said proximal end of said conduit;
   d. means to introduce a procoagulant to the blood vessel opening; and
   e. a seal consisting of an elastomeric material continuously and adhereingly disposed in said conduit central lumen along a predetermined segment at said proximal end thereof, said seal permitting ingress and egress of fluid to and from said conduit lumen via a syringe.

2. A medical sealing apparatus for sealing a blood vessel aperture in a patient, comprising:
   (a) a vascular introducer member comprising:
      (i) a thin, substantially straight body,
      (ii) a central lumen of a predetermined inside diameter in said body, and
      (iii) a side port communicatively connected to said central lumen, said side port being for introduction of a procoagulant to said central lumen and to the blood vessel aperture; and
   (b) a vascular sealing member adapted for insertion into and retraction from said central lumen of said vascular introducer member, said vascular sealing member comprising:
      (i) a thin, straight, elongated conduit having an outside diameter slightly less than said vascular introducer member central lumen inside diameter, and a central lumen, said conduit having proximal and distal ends, said outside diameter being substantially uniform from said proximal end to said distal end, said conduit end being insertable into the blood vessel aperture and having an inflation segment including an external orifice which is communicatively connected to said lumen;
      (ii) an expandable member sealingly disposed at said conduit distal end inflation segment, said expandable member being inflatable to a predetermined diameter;
      (iii) a seal consisting of an elastomeric material disposed in said conduit central lumen at said proximal end thereof, said seal permitting ingress and egress of fluid to and from said conduit lumen via a syringe.

3. The medical sealing device of claim 1, wherein said conduit comprises hypotubing.

4. The medical sealing device of claim 1, wherein said inflation segment is a hollow tubular structure extending coaxially from said conduit distal end and having a predetermined outside diameter which is not greater than the diameter of said conduit at said distal end thereof, and a predetermined length, and wherein said central lumen is coextensive with said inflation segment.

5. The medical sealing device of claim 4, wherein said conduit and said inflation segment comprise a unitary structure constructed of a homogeneous substance.

6. The medical sealing device of claim 4, further comprising an atraumatic extension disposed at an outward end of said inflation segment opposite its point of connection with said conduit, said atraumatic extension being constructed of a flexible material.

7. The medical sealing device of claim 6, wherein said conduit, said inflation segment, and said atraumatic extension comprise a unitary structure constructed of a homogeneous substance.

8. The medical sealing device of claim 2, wherein said expandable member has a tubular configuration in an uninflated state with a tube wall and opposing tube ends, said tube ends being sealingly secured to said inflation segment.

9. The medical sealing device of claim 8, wherein said expandable member has a rounded configuration in an inflated state.

10. The medical sealing device of claim 8, wherein said expandable is a pneumatic member which is inflatable via a gas.

11. The medical sealing device of claim 8, wherein said expandable member is a hydraulic member which is inflatable via a liquid.

12. The medical sealing device of claim 8, wherein said expandable member has a diameter greater than the size of the patient body aperture which is being sealed.

13. The medical sealing device of claim 2, wherein:
   (i) said inflation segment is coaxially disposed from conduit distal end, and wherein said central lumen is coextensive with said extension member;
   (ii) said expandable member has a tubular configuration in an uninflated state with a tube wall and opposing tube ends, said tube ends, being sealingly secured to said inflation segment; and
   (iii) said expandable member has a rounded configuration in an inflated state.

14. The medical sealing device of claim 2, wherein said means to introduce a procoagulant releases procoagulant at said blood vessel aperture at a point proximally located with respect to said expandable member.

15. A medical, vascular sealing apparatus for closing an aperture in a patient blood vessel, consisting essentially of:
   (a) a sealing member, consisting essentially of:
      (i) a thin, straight, cylindrical elongated conduit having a predetermined outside diameter, and a central lumen, said conduit having proximal and distal ends, said outside diameter being uniform throughout its entire length from said proximal to said distal end, said conduit distal end being insertable into the patient body aperture and having an inflation segment including an external orifice which is communicatively connected to said lumen, said inflation segment coaxially extending from conduit distal end;

(ii) an expandable member sealingly disposed at said conduit distal end inflation segment, said expandable member being inflatable to a predetermined diameter; and (iii) an elastomeric sealing member for connection of said conduit lumen to an external inflation syringe, said sealing member being sealingly and adhereingly disposed in said conduit lumen at said proximal end thereof; and (b) a hemostasis valve-type introducer member having a body of a predetermined outside diameter and including a proximal hemostasis valve, a single longitudinal lumen in said body extending from and through said hemostasis valve and opening to an open distal insertion end, said lumen having a predetermined diameter which is slightly greater than said conduit outside diameter, said insertion end being adapted for location in the blood vessel aperture, a single, proximal, lateral fluid injection port communicatively connected to said introducer lumen, whereby said conduit is extended through said introducer lumen so that said expandable member is disposed outwardly beyond said introducer distal insertion end, said fluid injection port being adapted to receive procoagulant and distribute said procoagulant out said distal insertion end, and whereby said sealing member is slideable in said introducer member lumen throughout its entire length, including through said hemostasis valve, for proximal withdrawal of said introducer member over said sealing member without splitting said introducer member, so that the sealing member may remain at the vessel aperture.

16. A method for closing an aperture in a patient's blood vessel; comprising the steps of:

a. positioning a vascular introducer member in the patient's blood vessel aperture, said introducer member comprising:

(i) a thin, substantially straight body with an open proximal end and an open distal end, (ii) a central lumen of a predetermined inside diameter, disposed in said body, and (iii) a side port communicatively connected to said central lumen; said body distal end being disposed in the patient's blood vessel;

b. engaging a medical, vascular sealing member with said introducer member, said sealing member comprising:

(i) a thin, elongated conduit having an outside diameter slightly less than said introducer member central lumen inside diameter, and a central lumen, said conduit having proximal and distal ends, said outside diameter being uniform from said proximal end to said distal end, said conduit distal end being insertable into the patient body aperture and having an inflation segment including an external orifice which is communicatively connected to said lumen;

(ii) an expandable member sealingly disposed at said conduit distal end inflation segment, said expandable member being inflatable to a predetermined diameter; and (iii) a seal consisting of an elastomeric material disposed in said conduit central lumen at said proximal end;

said sealing member being inserted into said introducer member proximal end through said introducer member lumen and into the blood vessel aperture extending said conduit through said introducer lumen so that said expandable member is disposed outwardly beyond said introducer distal end;

c. inflating said expandable member by piercing said elastomeric seal with a syringe and injecting fluid therefrom;

d. moving said sealing member conduit through said introducer member lumen to bring said expandable member into contact with the blood vessel aperture;

e. depositing procoagulant at said patient blood vessel aperture for rapid closure by introducing procoagulant into said introducer member lumen though said introducer member side port and distributing said procoagulant out said distal end thereof while said sealing member expandable member is still inflated;

f. disengaging said sealing member from said introducer member by proximally sliding said introducer member over the entire length of said sealing member, including said proximal end thereof, so that the sealing member remains alone in the vessel aperture until the aperture is closed; and g. removing said sealing member.

* * * * *